(12) United States Patent
Campbell et al.

(10) Patent No.: US 6,977,319 B2
(45) Date of Patent: Dec. 20, 2005

(54) ALKYLATED AROMATIC COMPOSITIONS, ZEOLITE CATALYST COMPOSITIONS AND PROCESSES FOR MAKING THE SAME

(75) Inventors: Curt B. Campbell, Hercules, CA (US); Thomas V. Harris, Benicia, CA (US); Pierre Tequi, Breaute (FR); Jean-Louis Le Coent, Le Havre (FR)

(73) Assignees: Chevron Oronite Company LLC, San Ramon, CA (US); Chevron Oronite S.A., Gonfreville-l Orcher (FR)

( * ) Notice: Subject to any disclaimer, the term of this patent is extended or adjusted under 35 U.S.C. 154(b) by 105 days.

(21) Appl. No.: 10/799,907

(22) Filed: Mar. 12, 2004

(65) Prior Publication Data

US 2005/0202954 A1    Sep. 15, 2005

(51) Int. Cl.$^7$ .......... C07C 15/107; C07C 15/02
(52) U.S. Cl. .......... 585/455; 585/446; 585/467
(58) Field of Search .......... 585/446, 455, 585/467

(56) References Cited

U.S. PATENT DOCUMENTS

| | | |
|---|---|---|
| 3,094,383 A | 6/1963 | Dzierzanowski et al. |
| 3,119,660 A | 1/1964 | Howell et al. |
| 3,130,007 A | 4/1964 | Breck |
| 3,288,716 A | 11/1966 | Becraft et al. |
| 3,641,177 A | 2/1972 | Eberly, Jr. et al. |
| 3,764,533 A | 10/1973 | Hunt et al. |
| 3,777,008 A | 12/1973 | Rundell et al. |
| 3,929,672 A | 12/1975 | Ward |
| 4,185,040 A | 1/1980 | Ward et al. |
| 4,259,193 A | 3/1981 | Tirtiaux et al. |
| 4,395,372 A | 7/1983 | Kluttz et al. |
| 4,764,295 A | 8/1988 | Le Coent |
| 4,876,408 A | 10/1989 | Ratcliffe et al. |
| 4,916,096 A | 4/1990 | Hoek et al. |
| 5,026,941 A | 6/1991 | Oguri et al. |
| 5,112,506 A | 5/1992 | Marsh et al. |
| 5,118,896 A | 6/1992 | Steigelmann et al. |
| 5,175,135 A | 12/1992 | Lee et al. |
| 5,191,135 A | 3/1993 | Dwyer et al. |
| 5,243,116 A | 9/1993 | Lee et al. |
| 5,922,922 A | 7/1999 | Harris et al. |
| 5,939,594 A | 8/1999 | Le Coent |
| 6,031,144 A | 2/2000 | Campbell et al. |
| 6,337,310 B1 | 1/2002 | Campbell et al. |

OTHER PUBLICATIONS

S. Sivasanker, A. Thangaraj, "Distribution of Isomers in the Alkylation of Benzene with Long-Chain Olefins over Solid Acid Catalysts", *Journal of Catalysis*, 138, 386-390 (1992), no month.

*Primary Examiner*—Elizabeth D. Wood
(74) *Attorney, Agent, or Firm*—Sarita R. Kelley

(57) ABSTRACT

The present invention is directed to novel alkylated aromatic compositions, zeolite catalyst compositions and processes for making the same. The catalyst compositions comprise zeolite Y and mordenite zeolite having a controlled macropore structure. The present invention is also directed to the preparation of the catalyst compositions and their use in the preparation of novel alkylated aromatic compositions. The catalyst compositions of the present invention exhibit reduced deactivation rates during the alkylation process, thereby increasing the life of the catalysts.

16 Claims, No Drawings

ALKYLATED AROMATIC COMPOSITIONS, ZEOLITE CATALYST COMPOSITIONS AND PROCESSES FOR MAKING THE SAME

FIELD OF THE INVENTION

The present invention is directed to novel alkylated aromatic compositions, zeolite catalyst compositions and processes for making the same. The catalyst compositions comprise zeolite Y and mordenite zeolite having a controlled macropore structure. The present invention is also directed to the preparation of the catalyst compositions and their use in the preparation of novel alkylated aromatic compositions. The catalyst compositions of the present invention exhibit reduced deactivation rates during the alkylation process, thereby increasing the life of the catalysts.

BACKGROUND OF THE INVENTION

It is well known to catalyze the alkylation of aromatics with a variety of Lewis or Bronsted acid catalysts. Typical commercial catalysts include phosphoric acid/kieselguhr, aluminum halides, boron trifluoride, antimony chloride, stannic chloride, zinc chloride, onium poly(hydrogen fluoride), and hydrogen fluoride. Alkylation with lower molecular weight olefins, such as propylene, can be carried out in the liquid or vapor phase. For alkylations with higher olefins, such as $C_{16}$ olefins, the alkylations are done in the liquid phase, usually in the presence of hydrogen fluoride. Alkylation of benzene with higher olefins is especially difficult, and requires hydrogen fluoride treatment. However, hydrogen fluoride is not environmentally attractive.

The use of the above listed acids is extremely corrosive, thus requiring special handling and equipment. Also, the use of these acids might involve environmental problems. Another problem is that the use of these acids can give less than desirable control on the precise chemical composition of the product produced. Thus, it is preferable to use a safer, simpler catalyst, preferably in solid state. This simpler process would result in less capital investment, which would result in a less expensive product.

Solid crystalline aluminosilicate zeolite catalysts have been known to be effective for the alkylation of aromatics with olefins. Zeolitic materials which are useful as catalysts are usually inorganic crystalline materials that possess uniform pores with diameters in micropore range that is less than 20 angstroms. Zeolites occur naturally and may also be prepared synthetically. Synthetic zeolites include, for example, zeolites A, X, Y, L and omega. It is also possible to generate metaloaluminophosphates and metalosilicophosphates. Other materials, such as boron, gallium, iron or germanium, may also be used to replace the aluminum or silicon in the framework structure.

These zeolite catalyst materials are commercially available as fine crystalline powders for further modification to enhance their catalytic properties for particular applications. Processes for the further modification to enhance catalytic properties of the zeolite catalysts are well known in the art, such as forming the zeolite catalysts into shaped particles, exchanging the cations in the catalyst matrix, etc.

Forming zeolite powders into shaped particles may be accomplished by forming a gel or paste of the catalyst powder with the addition of a suitable binder material such as a clay, an inorganic compound, or an organic compound and then extruding the gel or paste into the desired form. Zeolite powders may also be formed into particles without the use of a binder. Typical catalyst particles include extrudates whose cross sections are circular or embrace a plurality of arcuate lobes extending outwardly from the central portion of the catalyst particles.

One problem with catalyst particles used in fixed bed reactors is catalyst deactivation. In most hydrocarbon conversion processes, including alkylation, the primary catalyst deactivation is caused by coke formation. This catalyst deactivation is a serious problem in the use of zeolite catalysts for alkylation reactions. This deactivation problem is well known in the art and it is well understood that the deactivation mechanism can involve polymerization of the olefin into large molecular species that cannot diffuse out of the pores containing the active sites in the zeolitic material.

The use of zeolite catalysts for preparation of alkyl aromatics is typically conducted by the catalytic alkylation of aromatic hydrocarbons with normal alpha olefins or branched-chain olefins, and optionally a promotor. The alkylated aromatic hydrocarbons can be converted into corresponding sulfonic acids which can be further converted into alkylated aromatic sulfonates.

A number of patents have discussed processes for the preparation of zeolite catalysts and the further shaping and forming of the catalyst particles and extrudates with and without the use of binders. There are also a number of patents disclosing the use of zeolite catalysts for alkylation of aromatic hydrocarbons.

U.S. Pat. No. 3,094,383 discloses the preparation of synthetic zeolite materials which upon hydration yield a sorbent of controlled effective pore diameter and in which the sorbent and its zeolite precursor are provided directly in the form of an aggregate.

U.S. Pat. No. 3,130,007 discloses the method of preparing sodium zeolite Y with silica to alumina ratios ranging from greater than 3 to about 3.9.

U.S. Pat. No. 3,119,660 discloses a process for making massive bodies or shapes of crystalline zeolites. The patent also discloses methods for the identification of the catalyst materials using X-ray powder diffraction patterns in conjunction with chemical analyses.

U.S. Pat. No. 3,288,716 discloses that the high "heavy content" of the alkylated aromatic product can be controlled during the alkylation step and has advantages over distilling the alkylated aromatic product to obtain the desired molecular weight.

U.S. Pat. Nos. 3,641,177 and 3,929,672 disclose the technique to remove sodium or other alkali metal ions from zeolite catalysts. The '177 patent also discloses that such removal of the sodium or other alkali metal ions activates the zeolite catalysts for the alkylation of aromatic hydrocarbons with olefins by liquid phase reaction.

U.S. Pat. Nos. 3,764,533, 4,259,193 and 5,112,506 disclose the "heavy alkylate" content influences neutral sulfonates and overbased sulfonates. In U.S. Pat. No. 5,112,506, the effect of molecular weight distribution or "heavy alkylate" is shown to influence the performance of both Neutral and HOB sulfonates and the di-alkylate content is shown to influence the rust performance of the corresponding sulfonate in U.S. Pat. No. 3,764,533. In U.S. Pat. No. 4,259,193, a mono-alkylate sulfonate is preferred. U.S. Pat. Nos. 3,288,716; 3,764,533; 4,259,193; and 5,112,506 are hereby incorporated by reference for all purposes.

U.S. Pat. No. 3,777,006 discloses the use of nucleating centers for the crystallization of crystalline aluminosilicate zeolites having a size in excess of 200 microns and characterized by high strength and excellent adsorptive properties.

U.S. Pat. No. 4,185,040 discloses the preparation of highly stable and active catalysts for the alkylation of aromatic hydrocarbons with $C_2$–$C_4$ olefins. The catalysts are acidic crystalline aluminosilicate zeolites which exhibit much improved deactivation rates.

U.S. Pat. No. 4,395,372 discloses an alkylation process for alkylating benzene comprising contacting benzene and lower olefins with a rare earth exchanged X or Y zeolite catalyst in the presence of sulfur dioxide.

U.S. Pat. No. 4,570,027 discloses the use of a low crystallinity, partially collapsed zeolite catalyst for producing alkylaromatic hydrocarbons. The alkylation reaction also involves conditioning the catalyst bed with hydrogen prior to conducting the alkylation reaction.

U.S. Pat. Nos. 4,762,813; 4,767,734; 4,879,019 and 5,111,792 disclose the preparation of a hydrocarbon conversion catalyst using a low silica to alumina ratio zeolite Y bound into an extrudate and steamed to modify the catalyst.

U.S. Pat. No. 4,764,295 discloses a process for making non-foaming detergent-dispersant lubricating oil additives. The process further involves carbonation for making the products more basic.

U.S. Pat. No. 4,876,408 discloses an alkylation process using an ammonium-exchanged and steam stabilized zeolite Y catalyst having an increased selectivity for mono-alkylation. The process involves the presence of at least one organic compound under conditions such that sufficient amount of carbonaceous material evenly deposits on the alkylation catalyst to substantially suppress its alkylation activity.

U.S. Pat. No. 4,891,448 discloses a process for alkylation of polycyclic aromatic compounds in the presence of an acidic mordenite zeolite catalyst having a silica to alumina molar ratio of at least 15:1 to produce a mixture of substituted polycyclic aromatic compounds enriched in the para alkylated isomers.

U.S. Pat. No. 4,916,096 discloses use of a zeolite Y catalyst for hydroprocessing. The zeolite Y catalyst comprises a modified crystalline aluminosilicate zeolite Y, a binder and at least one hydrogenation component of a Group VI or a Group VIII metal.

U.S. Pat. No. 5,004,841 discloses a process for alkylation of polycyclic aromatic compounds in the presence of an acidic mordenite zeolite catalyst having a silica to alumina molar ratio of at least 15:1 to produce substituted polycyclic aromatic compounds enriched in the linear alkylated isomers.

U.S. Pat. No. 5,026,941 discloses the use of a zeolite Y catalyst having a silica to alumina ratio of 15 to 110 for the alkylation of naphthalene or mono-isopropylnaphthalene.

U.S. Pat. No. 5,118,896 discloses an aromatic alkylation process comprising the steps of contacting a hydrocarbon feed with an alkylating agent under liquid phase alkylation conditions in the presence of a silica-containing large macropore, small particle size zeolite catalyst, the catalyst having a pore volume of about 0.25 to 0.50 cc/g in pores having a radius of 450 angstroms and a catalyst particle diameter of not more than 1/32 of an inch.

U.S. Pat. No. 5,175,135 discloses the use of an acidic mordenite zeolite catalyst for alkylation of aromatic compounds with an alkylating agent having from one carbon atom to eight carbon atoms to produce substituted aromatic compounds enriched in the linear alkylated isomers. The acidic mordenite catalyst is characterized by its silica to alumina molar ratio, its porosity and a Symmetry Index.

U.S. Pat. No. 5,191,135 discloses the process for making long-chain alkyl-substituted aromatic compounds from naphthalenes, the process comprising a zeolite alkylation catalyst in the presence of 0.5 to 3.0 weight percent water. The presence of water increases the selectivity for making mono-alkylated products.

U.S. Pat. Nos. 5,240,889 and 5,324,877 disclose processes for the preparation of a catalyst composition having alkylation and/or transalkylation activity and wherein the catalyst composition contains greater than 3.5 weight percent water based on the total weight of the catalyst composition and the aromatic alkylation process using said catalyst composition and olefins containing 2 carbon atoms to 25 carbon atoms.

U.S. Pat. No. 5,198,595 discloses a process for alkylation of benzene or substituted benzene in the presence of an acidic mordenite zeolite catalyst having a silica to alumina ratio of at least 160:1 and a Symmetry Index above about 1.0. A process for the preparation of the catalyst is also disclosed.

U.S. Pat. No. 5,243,116 discloses the production of alkylated benzenes by alkylation and/or transalkylation in the presence of an acidic mordenite zeolite catalyst having a silica to alumina molar ration of at least 30:1 and a specific crystalline structure determined by X-ray diffraction.

U.S. Pat. No. 5,453,553 discloses a process for the production of linear alkyl benzenes which process comprises co-feeding a mixture of benzene, linear olefins and molecular hydrogen in the presence of a zeolite catalyst containing a transition metal under alkylation condition such that the catalyst is not deactivated.

U.S. Pat. No. 5,506,182 discloses the preparation of a catalyst composition comprising 10 to 90 percent of a modified zeolite Y catalyst formed from a modified zeolite Y and 10 to 90 percent binder using slurries of the modified zeolite Y and the binder to form the catalyst composition having a clear absorption peak in an IR spectrum of a wavelength of 3602 per centimeter. The patent also discloses the substitution of iron for the alumina in the zeolite Y structure.

U.S. Pat. No. 5,922,922 discloses a process for isomerizing a normal alpha olefin in the presence of an acidic catalyst having a one-dimensional pore system, and then using the isomerized olefin to alkylate aromatic hydrocarbons in the presence of a second acidic catalyst, which can be zeolite Y having a silica to alumina ratio of at least 40 to 1.

U.S. Pat. No. 5,939,594 discloses the preparation of a superalkalinized alkylaryl sulfonate of alkaline earth metal. The alkyl group of the alkylaryl sulfonate contains between 14 to 40 carbon atoms and the aryl sulfonate radical of alkaline earth metal is fixed in a molar proportion comprised between 0 and 13% in positions 1 or 2 of the linear alkyl chain.

U.S. Pat. No. 6,031,144 discloses a process for reducing the residual olefin content of an alkylation reaction product by removing at least a portion of the non-alkylated single-ring aromatic hydrocarbon and then reacting the remaining alkylation reaction product in the presence of an acidic catalyst such as a molecular sieve or clay.

U.S. Pat. No. 6,337,310 discloses the preparation of alkylbenzene from preisomerized normal alpha olefins for making low overbased and high overbased sulfonates having a TBN in the range of 3 to 500. The process uses HF as catalyst or a solid acidic alkylation catalyst, such as a zeolite having an average pore size of at least 6 angstroms.

U.S. Pat. No. 6,525,234 discloses a process for alkylating aromatic using a porous crystalline material, e.g., MCM-22 and in situ regenerating the catalyst by use of a polar compound having a dipole moment of at least 0.05 Debyes.

It is known that most solid acid catalysts produce high 2-aryl attachment when alkylating with alpha-olefins. See S. Sivasanker, A. Thangaraj, "Distribution of Isomers in the Alkylation of Benzene with Long-Chain Olefins over Solid Acid Catalysts," *Journal of Catalysis,* 138, 386–390 (1992). This is especially true for mordenite zeolite.

Two general treatises on zeolite are: *Handbook of Molecular Sieves* by Rosemarie Szostak (Van Nostrand Reinhold, New York 1992) and *Molecular Sieves: Principles of Synthesis and Identification,* $2^{nd}$ Edition, by Rosemarie Szostak (Chapman and Hall, London, UK 1999).

SUMMARY OF THE INVENTION

The present invention is directed to novel alkylated aromatic compositions and processes for preparation of carbonated, overbased alkylated aromatic sulfonates, which processes comprise the alkylation in the presence of the catalyst composites of this invention, and further sulfonation and carbonation, overbasing of the alkylated aromatic sulfonic acids.

The present invention is also directed to zeolite catalyst compositions having a controlled macropore structure comprising zeolite Y and mordenite zeolite. The present invention is also directed to a process for preparing the catalyst compositions. The catalysts and catalyst compositions exhibits reduced deactivation rates during the alkylation process, thereby increasing the life of the catalysts and the catalyst compositions.

In particular, the present invention is directed to an alkylated aromatic composition comprising a mixture of:

(a) an alkylated aromatic hydrocarbon alkylation product wherein the alkylation reaction is conducted in the presence of an alkylation catalyst having a macropore structure comprising zeolite Y, and wherein the peak macropore diameter of the catalyst, measured by ASTM Test No. D 4284-03, is less than or equal to about 2000 angstroms and the cumulative pore volume of the catalyst at pore diameters less than or equal to about 500 angstroms, measured by ASTM Test No. D 4284-03, is less than or equal to about 0.30 milliliters per gram; and (b) an alkylated aromatic hydrocarbon alkylation product wherein the alkylation reaction is conducted in the presence of an alkylation catalyst having a macropore structure comprising mordenite zeolite having a silica to alumina molar ratio of about 50 to about 105 and wherein the peak macropore diameter of the catalyst, measured by ASTM Test No. D 4284-03, is less than or equal to about 900 angstroms and the cumulative pore volume of the catalyst at pore diameters less than or equal to about 500 angstroms, measured by ASTM Test No. D 4284-03, is less than or equal to about 0.30 milliliters per gram.

The weight percent of the alkylated aromatic hydrocarbon of (a) in the mixture may be in the range of about 40 percent to about 99 percent based on the total alkylated aromatic composition. Preferably the weight percent of the alkylated aromatic hydrocarbon of (a) in the mixture is in the range of about 50 percent to about 90 percent based on the total alkylated aromatic composition, and more preferably the weight percent of the alkylated aromatic hydrocarbon of (a) in the mixture is in the range of about 70 percent to about 80 percent based on the total alkylated aromatic composition.

The alkyl groups of the alkylated aromatic composition may be derived from alpha olefins, isomerized olefins, branched-chain olefins, or mixtures thereof. The alpha olefins or the isomerized olefins have from about 6 carbon atoms to about 40 carbon atoms. Preferably, the alpha olefins or the isomerized olefins have from about 20 carbon atoms to about 40 carbon atoms. The branched-chain olefins have from about 6 carbon atoms to about 70 carbon atoms. Preferably, the branched-chain olefins have from about 8 carbon atoms to about 50 carbon atoms. More preferably, the branched-chain olefins have from about 12 carbon atoms to about 18 carbon atoms.

The alkyl groups of the alkylated aromatic composition may be partially-branched-chain isomerized olefins wherein the olefins have from about 6 carbon atoms to about 40 carbon atoms. Preferably, the partially-branched-chain isomerized olefins have from about 20 carbon atoms to about 40 carbon atoms.

The aromatic hydrocarbon of the alkylated aromatic composition may be benzene, toluene, xylene, cumene, or mixtures thereof. Preferably, the aromatic hydrocarbon is toluene or benzene.

The zeolite Y in step (a) and the mordenite zeolite in step (b) may contain a binder. Preferably, the binder in the zeolite Y in step (a) and the binder in the mordenite zeolite in step (b) is alumina.

The zeolite Y in step (a) and the mordenite zeolite in step (b) may be in the form of a tablet.

Another embodiment of the present invention is directed to a process for preparing an alkylated aromatic composition comprising:

(a) contacting at least one aromatic hydrocarbon with at least one olefin under alkylation conditions in the presence of a zeolite catalyst having a macropore structure comprising zeolite Y, and wherein the peak macropore diameter of the catalyst, measured by ASTM Test No. D 4284-03, is less than or equal to about 2000 angstroms and the cumulative pore volume of the catalyst at pore diameters less than or equal to about 500 angstroms, measured by ASTM Test No. D 4284-03, is less than or equal to about 0.30 milliliters per gram to form a first alkylated aromatic hydrocarbon product;

(b) contacting at least one aromatic hydrocarbon with at least one olefin under alkylation conditions in the presence of a zeolite catalyst having a macropore structure comprising mordenite zeolite having a silica to alumina molar ratio of about 50 to about 105, and wherein the peak macropore diameter of the catalyst, measured by ASTM Test No. D 4284-03, is less than or equal to about 900 angstroms and the cumulative pore volume of the catalyst at pore diameters less than or equal to about 500 angstroms, measured by ASTM Test No. D 4284-03, is less than or equal to about 0.30 milliliters per gram to form a second alkylated aromatic hydrocarbon product; and (c) combining the first alkylated aromatic hydrocarbon product and the second alkylated aromatic hydrocarbon product to form the alkylated aromatic composition;

wherein steps (a) and (b) can be conducted in any order.

The above process may further comprise in step (b) the reactivation of the deactivated zeolite catalyst with a suitable solvent flush, preferably the solvent is an aromatic hydrocarbon. More preferably, the aromatic hydrocarbon is benzene.

The above process may further comprise sulfonating the alkylated aromatic composition to form an alkylated aromatic sulfonic acid. The alkylated aromatic sulfonic acid may be reacted with an alkaline earth metal and carbon dioxide to produce a carbonated, overbased alkylated aromatic sulfonate.

The first alkylated aromatic hydrocarbon product in the alkylated aromatic composition may be in the range of about 40 percent to about 99 percent based on the total alkylated aromatic composition. Preferably, the first alkylated aromatic hydrocarbon product in the alkylated aromatic composition is in the range of about 50 percent to about 90 percent based on the total alkylated aromatic composition. More preferably, the first alkylated aromatic hydrocarbon product in the alkylated aromatic composition is in the range of about 70 percent to about 80 percent based on the total alkylated aromatic composition.

The olefin in step (a) and step (b) may be independently an alpha olefin, an isomerized olefin, a branched-chain olefin, or mixtures thereof. The alpha olefin or isomerized olefin may have from about 6 carbon atoms to about 40 carbon atoms. Preferably, the alpha olefin or isomerized olefin has from about 20 carbon atoms to about 40 carbon atoms. The branched-chain olefin may have from about 6 carbon atoms to about 70 carbon atoms. Preferably, the branched-chain olefin has from about 8 carbon atoms to about 50 carbon atoms. More preferably, the branched-chain olefin has from about 12 carbon atoms to about 18 carbon atoms.

The olefin in step (a) or step (b) may be independently a partially-branched-chain isomerized olefin, and the olefin may have from about 6 carbon atoms to about 40 carbon atoms. Preferably, the partially-branched-chain isomerized olefin has from about 20 carbon atoms to about 40 carbon atoms.

The aromatic hydrocarbon of the alkylated aromatic composition may be benzene, toluene, xylene, cumene, or mixtures thereof. Preferably, the aromatic hydrocarbon is toluene or benzene.

The cumulative pore volume of the zeolite catalyst at pore diameters less than or equal to about 400 angstroms in step (a) and step (b) is less than or equal to about 0.30 milliliters per gram. Preferably, cumulative pore volume of the zeolite catalysts at pore diameters less than or equal to about 300 angstroms in steps (a) and (b) is less than about 0.25 milliliters per gram, more preferably at pore diameters less than or equal to about 300 angstroms is less than about 0.20 milliliters per gram, and most preferably at pore diameters less than or equal to about 300 angstroms is in the range of about 0.08 milliliters per gram to about 0.16 milliliters per gram.

The cumulative pore volume of the zeolite catalysts at pore diameters less than or equal to about 400 angstroms in steps (a) and (b) is in the range of about 0.05 milliliters per gram to about 0.18 milliliters per gram. Preferably, the cumulative pore volume of the zeolite catalysts at pore diameters less than or equal to about 300 angstroms in steps (a) and (b) is in the range of about 0.08 milliliters per gram to about 0.16 milliliters per gram.

The zeolite Y catalyst in step (a) has a peak macropore diameter in the range of about 700 angstroms to about 1800 angstroms. Preferably, the peak macropore diameter of the zeolite Y catalyst in step (a) is in the range of about 750 angstroms to about 1600 angstroms. More preferably, the peak macropore diameter of the zeolite Y catalyst in step (a) is in the range of about 900 angstroms to about 1400 angstroms.

In step (b), the peak macropore diameter of the mordenite zeolite catalyst is in the range of about 400 angstroms to about 800 angstroms. Preferably in step (b), the peak macropore diameter of the mordenite zeolite catalyst is in the range of about 400 angstroms to about 700 angstroms. More preferably in step (b), the peak macropore diameter of the mordenite zeolite catalyst is in the range of about 450 angstroms to about 600 angstroms.

In steps (a) in the above process, the zeolite Y catalyst has a silica to alumina ratio of about 5:1 to about 100:1. Preferably in step (a), the zeolite Y catalyst has a silica to alumina ratio of about 30:1 to about 90:1. More preferably in step (a), the zeolite Y catalyst has a silica to alumina ratio of about 60:1 to about 80:1.

In step (b) in the above process, preferably the mordenite zeolite catalyst has a silica to alumina ratio of about 60:1 to about 80:1.

The zeolite Y in step (a) and the mordenite zeolite in step (b) may contain a binder. Preferably, the binder in the zeolite Y in step (a) and the binder in the mordenite zeolite in step (b) is alumina.

The zeolite Y in step (a) and the mordenite zeolite in step (b) may be in the form of a tablet.

A further embodiment of the present invention is directed to a process for preparing an alkylated aromatic composition comprising contacting at least one aromatic hydrocarbon with at least one olefin in the presence of a zeolite catalyst having a macropore structure comprising zeolite Y and mordenite zeolite having a silica to alumina ratio of about 50:1 to about 105:1, and wherein the peak macropore diameter of the catalyst, measured by ASTM Test No. D 4284-03, is less than or equal to about 2000 angstroms and the cumulative pore volume of the catalyst at pore diameters less than or equal to about 500 angstroms, measured by ASTM Test No. D 4284-03, is less than or equal to about 0.30 milliliters per gram.

The cumulative pore volume of the zeolite catalyst at pore diameters less than or equal to about 400 angstroms is less than or equal to about 0.30 milliliters per gram. Preferably, the cumulative pore volume zeolite catalyst at pore diameters less than or equal to about 300 angstroms is less than or equal to about 0.25 milliliters per gram. More preferably, the cumulative pore volume zeolite catalyst at pore diameters less than or equal to about 300 angstroms is less than or equal to about 0.20 milliliters per gram.

The cumulative pore volume of the zeolite catalyst at pore diameters less than or equal to about 400 angstroms may be in the range of about 0.05 milliliters per gram to about 0.18 milliliters per gram. Preferably, the cumulative pore volume of the zeolite catalyst at pore diameters less than or equal to about 300 angstroms is in the range of about 0.08 milliliters per gram to about 0.16 milliliters per gram.

The peak macropore diameter of the zeolite catalyst is in the range of about 400 angstroms to about 1500 angstroms. Preferably, the peak macropore diameter of the zeolite catalyst is in the range of about 500 angstroms to about 1300 angstroms. More preferably the peak macropore diameter of the zeolite catalyst is in the range of about 600 angstroms to about 1100 angstroms, and most preferably the peak macropore diameter of the zeolite catalyst is in the range of about 750 angstroms to about 900 angstroms.

The zeolite Y has a silica to alumina molar ratio of about 5:1 to about 100:1 and the mordenite zeolite has a silica to alumina molar ratio of about 50:1 to about 105:1. Preferably the zeolite Y has a silica to alumina molar ratio of about 30:1 to about 90:1, and more preferably the zeolite Y and the mordenite zeolite independently has a silica to alumina molar ratio of about 60:1 to about 80:1.

The zeolite catalyst may contain a binder. Preferably, the binder is alumina.

The zeolite catalyst may be in the form of a tablet.

Yet another embodiment of the present invention is directed to a zeolite catalyst composition having a macropore structure comprising:

(a) zeolite Y; and
(b) mordenite zeolite having a silica to alumina molar ratio in the range of about 50:1 to about 105:1;

wherein the peak macropore diameter of the catalyst composition, measured by ASTM Test No. D 4284-03, is less than about 2000 angstroms and the cumulative pore volume of the catalyst at pore diameters less than or equal to about 500 angstroms, measured by ASTM Test No. D 4284-03, is less than or equal to about 0.30 milliliters per gram.

The cumulative pore volume of the zeolite catalyst composition at pore diameters less than or equal to about 400 angstroms is less than or equal to about 0.30 milliliters per gram. Preferably, the cumulative pore volume zeolite catalyst composition at pore diameters less than or equal to about 300 angstroms is less than or equal to about 0.25 milliliters per gram. More preferably, the cumulative pore volume zeolite catalyst composition at pore diameters less than or equal to about 300 angstroms is less than or equal to about 0.20 milliliters per gram.

The cumulative pore volume of the zeolite catalyst composition at pore diameters less than or equal to about 400 angstroms may be in the range of about 0.05 milliliters per gram to about 0.18 milliliters per gram. Preferably, the cumulative pore volume of the zeolite catalyst composition at pore diameters less than or equal to about 300 angstroms is in the range of about 0.08 milliliters per gram to about 0.16 milliliters per gram.

The peak macropore diameter of the zeolite catalyst composition is in the range of about 400 angstroms to about 1500 angstroms. Preferably, the peak macropore diameter of the zeolite catalyst composition is in the range of about 500 angstroms to about 1300 angstroms. More preferably the peak macropore diameter of the zeolite catalyst composition is in the range of about 600 angstroms to about 1100 angstroms, and most preferably the peak macropore diameter of the zeolite catalyst composition is in the range of about 750 angstroms to about 900 angstroms.

The zeolite Y in step (a) having a silica to alumina ratio of about 5:1 to about 100:1, preferably the zeolite Y has a silica to alumina molar ratio of about 30:1 to about 90:1, and more preferably the zeolite Y has a silica to alumina molar ratio of about 60:1 to about 80:1.

The mordenite zeolite in step (b) preferably has a silica to alumina molar ratio of about 60:1 to about 80:1.

The zeolite catalyst composition may contain a binder. Preferably, the binder is alumina.

The zeolite catalyst composition may be in the form of a tablet.

DETAILED DESCRIPTION OF THE INVENTION

Definitions

The term "alkylate" means an alkylated aromatic hydrocarbon.

The term "2-aryl content" is defined as the percentage of total alkylate (the alkylate species in which the alkyl chain derived from the olefin employed in the present alkylation process is attached to the aromatic ring) that is comprised of those chemical species in which the attachment of the alkyl chain to the aromatic ring is at the 2-position along the alkyl chain.

The term "binder" means any suitable inorganic material which can serve as matrix or porous matrix to bind the zeolite particles into a more useful shape.

The term "branched-chain olefins" means olefins derived from the polymerization of olefin monomers higher than ethylene and containing a substantial number of branches wherein the branches are alkyl groups having from about one carbon atom to about 30 carbon atoms. Mixtures of ethylene and higher olefins are also contemplated.

The term "calcining" as used herein means heating the catalyst to about 400° C. to about 1000° C. in a substantially dry environment.

The term "carbonated, overbased" is used to describe those alkaline earth metal alkyl aromatic sulfonates in which the ratio of the number of equivalents of the alkaline earth metal moiety to the number of equivalents of the aromatic sulfonic acid moiety is greater than one, and is usually greater than 10 and may be as high as 20 or greater.

The term "cumulative pore volume" obtained by Mercury Intrusion Porosimetry as used herein refers to that part of the total volume in milliliters per gram derived from the graphical, cumulative pore volume distribution, measured by Section 14.1.6 of ASTM D 4284-03, or the corresponding tabular presentation of the same data between defined upper and lower pore diameters. When no lower diameter limit is defined, the lower limit is the lowest detection limit or lowest radius measured by Section 14.1.6 of ASTM D 4284-03.

The terms "dry basis", "anhydrous basis", and "volatiles-free basis" shall refer to the dry weight of catalyst composite or raw materials expressed on a metal oxides basis such as $Na_2O \cdot Al_2O_3 \cdot xSiO_2$.

The term "flush" as used herein means contacting the deactivated mordenite catalysts and mordenite catalyst composites of this invention in the reactor with a suitable solvent, such as an aromatic hydrocarbon for reactivation of the mordenite catalysts and mordenite catalyst composites.

The term "loss-on-ignition (LOI)" as used herein means the percent weight loss of the zeolite composite and raw material samples which volatilize or evaporate when heated to 538° C. for 1 hour. When the temperature is greater than or equal about 538° C., the "loss-on-ignition" approximates the percent volatiles.

The terms "macropore", "mesopore", and "micropore" as used herein follow the definitions set forth by the International Union of Pure and Applied Chemistry (IUPAC), Division of Physical Chemistry, in Manual of Symbols and Terminology for Physicochemical Quantities and Units, Appendix II Definitions, Terminology and Symbols in Colloid and Surface Chemistry Part I, Adopted by the IUPAC Council at Washington, D.C., USA, on 23 Jul., 1971. Pores with widths or diameters exceeding ~50 nanometers (500 angstroms) are called "macropores". Pores with widths or diameters not exceeding ~2.0 nanometers (20 angstroms) are called "micropores". Pores of intermediate size (2.0 nanometers<width or diameter≦50 nm) are called "mesopores".

The term "Mercury Intrusion Porosimetry" refers to the ASTM Test No. D 4284-03 used to determine pore volume distribution of catalysts by Mercury Intrusion Porosimetry. Mercury pore distribution was measured using a Quantachrome Scanning Mercury Porosimeter Model SP-100. The software version used by the instrument is V2.11 (dated Oct.

27, 1993). Surface tension used in the calculation is 473 dynes per centimeter and the contact angle is 140 degrees.

The terms "normal alpha olefin" and "linear alpha olefin" mean those straight-chain olefins without a significant degree of alkyl branching in which the carbon to carbon double bond resides primarily at the end or "alpha" position of the carbon chain, i.e., between $C_1$ and $C_2$. Normal alpha olefins are derived from polymerization of ethylene.

The term "normal alpha olefin isomerization" means the conversion of normal alpha olefins into isomerized olefins having a lower alpha olefin content (the double bond is between $C_1$ and $C_2$), higher internal olefin content (the double bond is in positions other than between $C_1$ and $C_2$), and optionally a higher degree of branching.

The term "partially-branched chain olefin" is defined as the olefin product of isomerization of normal alpha olefins wherein the degree of branching is higher than in the starting normal alpha olefins.

The term "peak macropore diameter" as used herein means the peak diameter (i.e., the diameter within the macropore region at which the differential plot of pore size distribution, as defined by Section 14.2, reaches a maximum) in the macropore range determined by ASTM Test No. 4284-03 for the macropore peak in the catalysts of the present invention.

The term "peptizing" means the dispersion of large aggregates of binder particles, including hydrated aluminas, into much smaller primary particles by the addition of acid.

The term "percent volatiles" as used herein means the difference between the actual weight of the catalyst composite or the raw materials and the weight of the material on a dry, anhydrous, or volatiles-free basis, expressed as a percentage of the actual sample weight.

The term "SAR" or "silica to alumina ratio" refers to the molar ratio of silicon oxide to aluminum oxide; mol $SiO_2$: mol $AlO_3$.

The term "sufficient water to shape the catalyst material" means quantity of water required to make an acid peptized mixture of zeolite and alumina powders into an extrudable mass.

The term "tabletting" as used herein refers to the process of forming a catalyst aggregate from zeolite powder or a mixture of zeolite and binder powders by compressing the powder in a die.

The term "total pore volume" obtained by Mercury Intrusion Porosimetry as used herein refers to the total pore volume in milliliters per gram derived from the graphical, cumulative pore volume distribution (Section 14.1.6 of ASTM D 4284-03) or the corresponding tabular presentation of the same data.

As used herein, all percentages are weight percent, unless otherwise specified.

As noted above, the present invention is directed to novel alkylated aromatic compositions and their sulfonated and carbonated products. The alkylation of the aromatic hydrocarbons is carried out in the presence of the zeolite catalyst compositions of the present invention having a controlled macropore structure comprising zeolite Y and mordenite zeolite. The catalysts of the present invention were characterized by pore volume distribution obtained by Mercury Intrusion Porosimetry, ASTM Test No. D 4284-03. Mercury Intrusion Porosimetry provides a graph of cumulative pore volume (pv) versus pore diameter (pd). Mercury Intrusion Porosimetry also is used to determine the macropore peak diameter from the derivative, delta pv ($\Delta pv$) divided by delta pd ($\Delta pd$). The graphs are used to characterize the catalysts of the present invention.

The zeolite catalyst compositions were prepared using zeolite Y and mordenite zeolite. Zeolite Y and mordenite zeolite may also be combined to prepare zeolite catalyst compositions of the present invention. When the zeolite catalyst compositions contain both zeolite Y and mordenite zeolite, the zeolite catalyst composite may be prepared by mixing zeolite Y and mordenite zeolite powders before the binding and shaping steps. The zeolite Y CBV 760® and CBV 600® available from Zeolyst International having a nominal silica to alumina ratio of 60 and 6.7, respectively, may be used for preparing the zeolite catalyst compositions of this invention. However, zeolite Y having a silica to alumina ratio between 5 and 110 may be used for the preparation of the zeolite catalysts compositions of the present invention. The mordenite zeolite 90A® having a nominal silica to alumina ratio of 90, also available from Zeolyst International, may be used for preparing the zeolite catalyst compositions of this invention. Mordenite zeolite having a silica to alumina ratio of 50 to 105 may be used in the preparation of the zeolite catalyst compositions of this invention.

The catalysts of the present invention may be shaped or formed into tablets, extrudates or any other shape using procedures well known in the prior art. The preparation of extrudates requires the presence of a binder, such as alumina. The tabletted catalysts do not require the presence of a binder, but a binder may be present in a tabletted zeolite catalyst. The crystalline zeolite powder may be compressed to form a tablet. The tabletted catalysts of the present invention provide exceptionally low deactivation rates in alkylation reactions.

The alkylation of aromatic hydrocarbons with one or more olefins may be carried out in a fixed bed reactor in the presence of the zeolite catalysts compositions of the present invention comprising only zeolite Y, only mordenite zeolite, or both zeolite Y and mordenite zeolite. The alkylation process is conducted without the addition of water and using dried aromatic hydrocarbon and olefin feed. It is believed that the presence of water during the alkylation increases the deactivation rate of the catalysts of this invention. When the alkylation using zeolite Y and mordenite zeolite is carried out in separate fixed bed reactors, the alkylated aromatic hydrocarbons may be combined to obtain the desired amount of alpha olefins versus branched-chain olefins. Alkylation reactions using normal alpha olefins and zeolite catalysts compositions comprising only mordenite zeolite give predominantly alkylated aromatic hydrocarbons wherein the attachment of the of the alkyl chain to the aromatic ring is at the 2-position along the alkyl chain. On the other hand, alkylation reactions using zeolite catalysts compositions comprising only zeolite Y and normal alpha olefins give predominantly attachments at other than the 2-position along the alkyl chain.

The alkylation reaction may be carried out by any conventionally known process. The aromatic hydrocarbon is reacted with one or more olefins in the presence of a catalyst of the present invention under alkylation reaction conditions. The above alkylation process is conducted without the addition of water and using dried aromatic hydrocarbon and olefin feed. It is believed that the presence of water during the alkylation process increases the deactivation rate of the catalysts of this invention.

The aromatic hydrocarbon may be single-ring or double-ring, preferably the aromatic hydrocarbon is a single-ring aromatic hydrocarbon. The aromatic hydrocarbon may be an alkylated aromatic hydrocarbon, such as a mono-alkylated aromatic hydrocarbon, wherein the alkyl group has from about 4 carbon atoms to about 80 carbon atoms. When the aromatic hydrocarbon used is a mono-alkylated aromatic, the product of the alkylation reaction is a di-alkylated aromatic hydrocarbon.

The olefins useful for alkylation of the aromatic hydrocarbons may be linear-chain olefins or branched-chain olefins having from about 4 carbon atoms to about 80 carbon atoms. In addition, normal alpha olefins may be isomerized to obtain partially-branched-chain olefins for use in alkylation process of the present invention. These resulting partially-branched-chain olefins may be alpha-olefins, beta-olefins, internal-olefins, tri-substituted olefins, and vinylidene olefins.

Alkylated aromatic hydrocarbon sulfonic acids of the alkylated aromatic hydrocarbons of the present invention may be prepared by any known sulfonation reaction. The alkylated aromatic sulfonic acids may be further reacted with an alkaline earth metal and carbon dioxide to obtain carbonated, overbased alkylated aromatic sulfonates useful as detergents in lubricating oils. Carbonation may be carried out by any conventionally known process. The degree of overbasing may be controlled by changing the reaction conditions and the amount of the alkaline earth metal and carbon dioxide used in the carbonation process.

The novel alkylation compositions of the present invention may be obtained by conducting the alkylation reactions as described above in the presence of the zeolite catalyst compositions of the present invention prepared as described in Examples 1–4 below.

Procedure for Isomerization of Normal Alpha Olefins

The isomerization process may be carried out in batch or continuous mode. The process temperatures can range from 50° C. to 250° C. In the batch mode, a typical method is to use a stirred autoclave or glass flask, which may be heated to the desired reaction temperature. A continuous process is most efficiently carried out in a fixed bed process. Space rates in a fixed bed process can range from 0.1 to 10 or more weight hourly space velocity.

In a fixed bed process, the isomerization catalyst is charged to the reactor and activated or dried at a temperature of at least 150° C. under vacuum or flowing inert, dry gas. After activation, the temperature of the isomerization catalyst is adjusted to the desired reaction temperature and a flow of the olefin is introduced into the reactor. The reactor effluent containing the partially-branched, isomerized olefins is collected. The resulting partially-branched, isomerized olefins contain a different olefin distribution (alpha olefin, beta olefin, internal olefin, tri-substituted olefin, and vinylidene olefin) and branching content than the unisomerized olefin.

Procedure for Alkylation of Aromatic Hydrocarbons

Alkylation of aromatic hydrocarbons with normal alpha olefins, partially-branched-chain isomerized olefins, and branched-chain olefins may be carried out by any method known by a person skilled in the art.

The alkylation reaction is typically carried out with an aromatic hydrocarbon and an olefin in molar ratios from 1:15 to 25:1. Process temperatures can range from about 100° C. to about 250° C. The process is carried out without the addition of water. As the olefins have a high boiling point, the process is preferably carried out in the liquid phase. The alkylation process may be carried out in batch or continuous mode. In the batch mode, a typical method is to use a stirred autoclave or glass flask, which may be heated to the desired reaction temperature. A continuous process is most efficiently carried out in a fixed bed process. Space rates in a fixed bed process can range from 0.01 to 10 or more weight hourly space velocity.

In a fixed bed process, the alkylation catalyst is charged to the reactor and activated or dried at a temperature of at least 150° C. under vacuum or flowing inert, dry gas. After activation, the alkylation catalyst is cooled to ambient temperature and a flow of the aromatic hydrocarbon compound is introduced, optionally toluene. Pressure is increased by means of a back pressure valve so that the pressure is above the bubble point pressure of the aromatic hydrocarbon feed composition at the desired reaction temperature. After pressurizing the system to the desired pressure, the temperature is increased to the desired reaction temperature. A flow of the olefin is then mixed with the aromatic hydrocarbon and allowed to flow over the catalyst. The reactor effluent comprising alkylated aromatic hydrocarbon, unreacted olefin and excess aromatic hydrocarbon compound are collected. The excess aromatic hydrocarbon compound is then removed by distillation, stripping, evaporation under vacuum, or any other means known to those skilled in the art.

Procedure for Sulfonation of Alkylated Aromatic Hydrocarbons

Sulfonation of alkylated hydrocarbons may be carried out by any method known by a person skilled in the art.

The sulfonation reaction is typically carried out in a falling film tubular reactor maintained at about 65° C. The alkylated aromatic hydrocarbon is placed in the tube and sulfur trioxide diluted with nitrogen is added to the alkylated aromatic hydrocarbon. The molar ratio of alkylated aromatic hydrocarbon to sulfur trioxide is maintained at about 1.05:1. The resulting alkylated aromatic sulfonic acid may be diluted with about 10% 100 Neutral oil followed by thermal treatment with nitrogen bubbling at a rate of about 10 liters per kilogram of product and stirring while maintaining the temperature at about 85° C. until the desired residual sulfuric acid content is obtained (maximum of about 0.5%).

Procedure for Carbonation, Overbasing of Alkylated Aromatic Sulfonic Acids

Carbonation, overbasing of alkylaromatic sulfonic acids may be carried out by any method known by a person skilled in the art to produce alkylaromatic sulfonates.

Generally, the carbonation, overbasing reaction is carried out in a reactor in the presence of the alkylated aromatic sulfonic acid, diluent oil, an aromatic solvent, and an alcohol. The reaction mixture is agitated and alkaline earth metal and carbon dioxide are added to the reaction while maintaining the temperature between about 20° C. and 80° C.

The degree of carbonation, overbasing may be controlled by the quantity of the alkaline earth metal and carbon dioxide added to the reaction mixture, the reactants and the reaction conditions used during the carbonation process.

Reactivation of Deactivated Mordenite Zeolite Catalysts and Composites

Once the mordenite zeolite catalysts and catalyst composites are completely deactivated, the alkylation reaction stops because of the polymerization of the olefin into large molecular species that cannot diffuse out of the crystal micropores containing the active sites in the zeolitic material. However, reactor bed need not be changed to remove the deactivated mordenite zeolite catalysts and catalyst composites. The deactivated mordenite zeolite catalysts and catalyst composites are reactivated at the end of an alkylation run by stopping the olefin feed stream to the reactor and permitting the aromatic hydrocarbon stream to continue to be flushed through the reactor for a sufficient time, typically from about 12 hours to about 24 hours.

EXAMPLES

Example 1

Preparation of Zeolite Catalyst Composition 1

Zeolite Catalyst Composition 1 is prepared by mixing zeolite Y powder and mordenite zeolite powder available from Zeolyst International or any other commercial source. The zeolite Y and mordenite zeolite powders are mixed in any proportion based on the desired alkylated aromatic product.

As an example, zeolite Y catalyst powder is mixed with mordenite zeolite catalyst powder to obtain a final ratio of 85:15 in the final Zeolite Catalyst Composition.

Zeolite Catalyst Composition 1 is prepared by the following method:

Loss-on-ignition (LOI) is determined for samples of commercially available zeolite Y (CBV 760® and CBV 600®) and mordenite zeolite (CBV 90A®) available from Zeolyst International by heating the samples to 538° C. for 1 hour. The LOI obtained provides the percent volatiles in the zeolite Y and mordenite zeolite batches being used. The LOI of a commercial sample of Versal® hydrated aluminum oxide available from Sasol is also obtained by heating the samples to 538° C. for 1 hour. Next, based on the results obtained from the LOI of the zeolite Y, mordenite zeolite and the alumina powders the amount of alumina powder is weighed out to obtain 80% (volatile-free basis) zeolite content of the composite consists of 85% zeolite Y and 15% mordenite zeolite on a volatile-free basis.

The three dry powders are added to a Baker Perkins mixer and dry mixed for 4 minutes. The amount of concentrated (70.7%) nitric acid to give 0.7 weight % (based on 100% nitric acid) of the dry weight of the zeolite and the alumina powders is calculated. This amount of 70.7% nitric acid was weighed out and dissolved in deionized water.

The total amount of water and 70.7% nitric acid needed to obtain a final concentration of approximately 50% total volatiles is calculated as follows. Volatiles in the Y zeolite, mordenite zeolite and alumina powders is calculated. Nitric acid solution is considered to be 100% volatiles. Thus, the amount of deionized water that must be added is the difference between the final concentration of volatiles of 50% minus the total volatiles in the three powders.

Deionized water is added over a period of 5 minutes to the powders in the mixer using a peristaltic pump. The mixer is then stopped so that the walls of the mixer can be scraped down. Mixing is then resumed and the solution of nitric acid in water is added over 5 minutes using the peristaltic pump. At the end of acid addition, mixing is continued for a total time of 40 minutes, with occasional holds to allow for scraping the sides of the mixer. At the end of the mixing period, the percent volatiles are measured. Additional amounts of deionized water is added until the mixture appears extrudable and the percent volatiles are again measured.

The wet mixture is extruded through 1.27 millimeters, asymmetric quadrilobe die inserts, in a Bonnot extruder. The wet long cylindrical strands are dried at 121° C. for 8 hours. The long cylindrical strands are then broken to give extrudates with length to diameter ratio of 2:6. The extrudates are sieved and the portion larger than 1.0 millimeter is retained.

The extrudates are then calcined in a muffle furnace using the following temperature program:

The extrudates are heated to 593° C. over two hours, then held at 593° C. for ½ hour and next cooled to 204° C. A total weight of the extrudates is obtained.

Mercury Intrusion Porosimetry is used to characterize the extrudates. A peak macropore diameter in angstroms and a cumulative pore volume at diameters less than 300 angstroms is obtained from the Mercury Intrusion Porosimetry data.

The Zeolite Catalyst Composition is charged to a pilot plant reactor used for the alkylation of aromatic hydrocarbons. The reaction effluent of this reactor has greater than or equal to 99% conversion of the olefin feed stream. When benzene is used as the aromatic hydrocarbon and the alkylation reaction is conducted using the Zeolite Catalyst Composition, there is a much higher attachment of the alkyl chain to the aromatic ring at the 2-position along the alkyl chain in the alkylated benzene than when the zeolite Y catalyst composite is used alone in the alkylation reaction.

Excess benzene is removed by distillation, stripping or any other suitable means and the alkylated benzene is sulfonated using sulfonation procedures well known in the art. The alkyl benzene sulfonic acid is further carbonated with an alkaline earth metal and carbon dioxide.

Example 2

Preparation of Zeolite Y Catalyst Composite

Zeolite Y Catalyst Composite was prepared are described above in Example 1 using zeolite Y CBV 760® available from Zeolyst International.

Example 3

Preparation of Mordenite Zeolite Catalyst Composite

Mordenite Zeolite Catalyst Composite was prepared are described above in Example 1 using mordenite zeolite CBV 90A® available from Zeolyst International.

Example 4

Preparation of Zeolite Catalyst Composition 2

Zeolite Catalyst Composition 2 is prepared by mixing Zeolite Y Catalyst Composite and Mordenite Zeolite Catalyst Composite prepared in Examples 2 and 3. The Zeolite Y Catalyst Composite and Mordenite Zeolite Catalyst Composite are mixed in any proportion based on the desired alkylated aromatic product. As an example, Zeolite Y Catalyst Composite is mixed with Mordenite Zeolite Catalyst Composite to obtain a final ratio of 85:15 in the Zeolite Catalyst Composition 2.

The resulting Zeolite Catalyst Composition 2 is charged to a pilot plant reactor for the alkylation of aromatic hydrocarbons as described below in Example 5.

Example 5

Preparation of Alkylbenzene Compositions using Zeolite Y Catalyst Composite Typically, alkylation of aromatic hydrocarbons with normal alpha olefins, partially-branched-chain isomerized olefins and branched-chain olefins was carried out as described below:

A fixed bed reactor constructed from 15.54 millimeters Schedule 160 stainless steel pipe was used for this alkylation test. Pressure in the reactor was maintained by an appropriate back pressure valve. The reactor and heaters were constructed so that adiabatic temperature control could be maintained during the course of alkylation runs. A 192 gram bed of 850 micrometer to 2 millimeters Alundum particles was packed in the bottom of the reactor to provide a pre-heat zone. Next, 100 grams of a zeolite Y catalyst composite similar to the zeolite Y catalyst composite prepared in Example 2 above was charged to the fixed bed reactor. The reactor was gently vibrated during loading to give a maximum packed bulk density of catalyst in the reactor. Finally, void spaces in the catalyst bed were filled with 351 grams 150 micrometers Alundum particles as interstitial packing.

The reactor was then closed, sealed, and pressure tested under nitrogen. Next, the alkylation catalyst was dehydrated during 15 hours at 200° C. under a 20 liters per hour flow of nitrogen measured at ambient temperature and pressure and then cooled to 100° C. under nitrogen. Benzene was then introduced into the catalytic bed in an up-flow manner at a flow rate of 195 grams per hour. Temperature (under adiabatic temperature control) was increased to a start-of-run temperature of 182° C. (measured just before the catalyst bed) and the pressure was increased to 14.6 atmospheres.

When temperature and pressure had lined out at desired start-of-run conditions of 182° C. and 14.6 atmospheres, a feed mixture, consisting of benzene and $C_{20-24}$ NAO at a molar ratio of 10:1 and dried over activated alumina, was introduced in an up-flow manner. As the feed reached the catalyst in the reactor, reaction began to occur and internal catalyst bed temperatures increased above the inlet temperature. After about 8 hours on-stream, the reactor exotherm was 20° C. At 26 hours on-stream, the olefin conversion in the product was 99.1%. The run was stopped after 408 hours on-stream, although the run could have continued. At this time, the olefin conversion was 99.45%.

Alkylated aromatic hydrocarbon products containing excess benzene were collected during the course of the run. After distillation to remove excess aromatic hydrocarbon, analysis showed that greater than 99% conversion of olefin was achieved during the course of the run.

A fixed bed reactor was constructed from 15.54 millimeters Schedule 160 stainless steel pipe. Pressure in the reactor was maintained by an appropriate back pressure valve. The reactor and heaters were constructed so that adiabatic temperature control could be maintained during the course of alkylation runs. A small amount of 850 micrometer to 2 millimeters acid-washed Alundum was packed in the bottom of the reactor to provide a pre-heat zone. Next, 100 grams of whole alkylation extrudate catalyst was charged to the fixed bed reactor. Finally, void spaces in the catalyst bed were filled with 150 micrometers acid-washed Alundum interstitial packing. The zeolite Y or the mordenite zeolite alkylation catalyst was then dehydrated for at least 8 hours at 200° C. under a flow of nitrogen gas and then cooled to ambient temperature under nitrogen gas. Benzene was then introduced into the catalytic bed in an up-flow manner. Temperature (isothermal temperature control) and pressure were increased at start of run conditions. Normal operating pressure was 11.91 atmospheres. The initial temperature of approximately 150° C. was chosen so that the temperature in the catalytic bed increased under adiabatic temperature control to about 160° C. to about 175° C. When temperature and pressure had lined out at desired start-of-run conditions, the reactor system was switched to adiabatic temperature control. A dried feed mixture, consisting of olefin and benzene, was introduced in an up-flow manner. The benzene to olefin molar ratio was 10:1. As the reaction began to occur, temperature increased in the catalyst bed above the inlet temperature.

Alkylated benzene product containing excess benzene was collected during the course of the run. After distillation to remove excess benzene, analysis showed that greater than 99% conversion of olefin was achieved during the course of the run.

Example 6

Preparation of Alkylbenzene Compositions

Typically, alkylation of aromatic hydrocarbons with normal alpha olefins, partially-branched-chain isomerized olefins and branched-chain olefins was carried out as described below:

A fixed bed reactor was constructed from 15.54 millimeters Schedule 160 stainless steel pipe. Pressure in the reactor was maintained by an appropriate back pressure valve. The reactor and heaters were constructed so that adiabatic temperature control could be maintained during the course of alkylation runs. A bed of 170 grams of 850 micrometer to 2 millimeters Alundum particles was packed in the bottom of the reactor to provide a pre-heat zone. Next, 100 grams of mordenite catalyst composite similar to the mordenite catalyst composite prepared in Example 3 above was charged to the fixed bed reactor. Finally, void spaces in the catalyst bed were filled with 309 grams of 150 micrometers Alundum particles interstitial packing. The reactor was gently vibrated while charging catalyst and alundum to ensure a high packed bulk density. After charging, the reactor was closed, sealed, and the pressure was tested.

The alkylation catalyst was then heated to 200° C. under a 20 liters per hour flow of nitrogen measured at ambient temperature and pressure and dehydrated for 23 hours at 200° C. The catalyst bed was then cooled to 100° C. under nitrogen. Benzene was then introduced into the catalytic bed in an up-flow manner at a flow rate of 200 grams per hour. Temperature (under adiabatic temperature control) was increased to a start of run inlet temperature of 154° C. (measured just before the catalyst bed) and the pressure was increased to 12.66 atmospheres.

When temperature and pressure had lined out at desired start-of-run conditions of 154° C. and 12.66 atmospheres, a feed mixture, consisting of benzene and $C_{20-24}$ NAO at a molar ratio of 15:1 and dried over activated alumina, was introduced in an up-flow manner at 200 grams per hour. As the feed reached the catalyst in the reactor, reaction began to occur and internal catalyst bed temperatures increased above the inlet temperature. After about 8 hours on-stream, the reactor exotherm was 20° C. In the first 57 hours on-stream, the olefin conversion decreased from 100% to 98.8% (Run Period 1). At this point, the catalyst bed was flushed with benzene at 200 grams per hour during 18 hours. Following the benzene flush, the benzene and olefin feed flow was resumed. Inlet temperature was increased to 162° C. at 57 run hours. Feed was continued until 351 run hours (Run Period 2 from 57 to 351 run hours). Olefin conversion was initially 98.9% during Run Period 2 but declined to 98.1% at 321 run hours and further to 95.3% at 351 run hours. A second benzene flush was performed at 351 run hours during 17 hours. After the second benzene flush, feed flow was resumed again to start Run Period 3. Feed was continued until 550 run hours. Olefin conversion was initially 98.5% but declined to 98.3% at 519 run hours and to 97.0% at 550 run hours. A third benzene flush was done during a weekend. Feed flow was resumed after the third benzene flush to begin Run Period 4. At the beginning of Run Period 4, olefin conversion was 98.8% and at 942 run hours the olefin conversion was 98.4%. The run was stopped after 942 hours on-stream but could have continued longer.

Alkylated aromatic hydrocarbon products containing excess benzene were collected during the course of the run. After distillation to remove excess aromatic hydrocarbon, analysis showed that greater than 97% conversion of olefin was achieved during most of the course of the run.

Example 7

Preparation of Alkylbenzene Sulfonic Acids

A mixture of 85 weight % of the alkylated benzene prepared using the zeolite Y catalyst and 15 weight % of the alkylated benzene prepared using mordenite zeolite catalyst as in Examples 5 and 6 above was sulfonated by a concurrent stream of sulfur trioxide ($SO_3$) and air with in a tubular reactor (2 meters long, 1 centimeter inside diameter) in a down flow mode using the following conditions:

Reactor temperature was 60° C., $SO_3$ flow rate was 73 grams per hour, and alkylate flow rate was 327 grams per hour at a $SO_3$ to alkylate molar ratio of 1.05. The $SO_3$ was generated by passing a mixture of oxygen and sulfur dioxide ($SO_2$) through a catalytic furnace containing vanadium oxide ($V_2O_5$).

The resulting crude alkylbenzene sulfonic acid had the following properties based on the total weight of the product: weight % of $HSO_3$ was 15.61% and weight % of $H_2SO_4$ was 0.53.

The crude alkylbenzene sulfonic acid (1665 grams) was diluted with 83 grams of 100 Neutral diluent oil and placed in a 4 liter four-neck glass reactor fitted with a stainless steel mechanical agitator rotating at about 300 rpm, a condenser and a gas inlet tube (2 millimeters inside diameter) located just above the agitator blades for the introduction of nitrogen. The contents of the reactor were placed under vacuum (40 millimeters Hg) and the reactor was heated to 110° C. with stirring and nitrogen was bubbled through the mixture at about 30 liters per hour for about 30 minutes until the weight % of $H_2SO_4$ is less than about 0.3 weight %. This material is the final alkylbenzene sulfonic acid.

The final alkylbenzene sulfonic acid had the following properties based on the total weight of the product: weight % of $HSO_3$ was 14.95 and weight % of $H_2SO_4$ was 0.17.

Example 7

Preparation of Alkylbenzene Sulfonates

To a 5 liter four-neck glass reactor equipped with heating and cooling capability and fitted with a stainless steel mechanical agitator rotating at between 300 and 350 rpm, a gas inlet tube (2 millimeters inside diameter) located just above the agitator blades for the addition of $CO_2$, a distillation column and condenser under nitrogen gas was charged 129.4 grams of centrate.

The centrate was a mixture of the sludge fractions previously produced during the purification of high TBN carbonated, overbased synthetic sulfonates by centrifugation and decantation and was added to the reaction mixture of this example for recycling the contents of the centrate. The centrate had a TBN of 197 and contained approximately 73 grams of xylene solvent, 12 grams active calcium sulfonate, 9 grams calcium hydroxide and calcium carbonate, 8 grams of carbon dioxide, and 23 grams of 100 Neutral diluent oil.

Next, 40 grams of methanol, 207 grams of xylene solvent, 296.5 grams (0.59 mole) of the alkylbenzene sulfonic acid ($HSO_3$ was 14.95 weight % based on the total weight of the reaction mixture) from Example 6 above was charged to the reactor over 15 minutes at room temperature. A slurry of 160 grams (2.16 mole) of calcium hydroxide, 362 grams of xylene solvent and 94.2 grams of methanol was added to the reactor and the contents of the reactor were cooled to 25° C. Subsequently, 33 grams (0.79 mole) of $CO_2$ was added to the reactor through the gas inlet tube over 39 minutes while the temperature of the reactor increased to about 32° C. A second slurry composed of 160 grams (2.16 mole) of calcium hydroxide, 384 grams xylene solvent, and 131 grams of methanol was then added to the reactor concurrently with 0.9 grams of $CO_2$ over about 1 minute. Then 92 grams of $CO_2$ was added to the reactor over 64 minutes while the temperature of the reactor was increased from about 30° C. to about 41° C. A third slurry composed of 82 grams of oxide and 298 grams of xylene solvent was then charged to the reactor concurrently with 1.4 grams of $CO_2$ over about 1 minute. Next, 55 grams (1.25 mole) of $CO_2$ was added to the reactor over approximately 60 minutes while keeping the reactor temperature at approximately 38° C.

The water and methanol were then distilled from the reactor by first heating the reactor to 65° C. over about 40 minutes at atmospheric pressure and then to 93° C. over about 60 minutes at atmospheric pressure and then finally to 130° C. over about 30 minutes at atmospheric pressure. The temperature of the reactor was then decreased to 110° C. over about 60 minutes at atmospheric pressure and next then cooled to approximately 30° C. and 475.7 grams of 600 Neutral diluent oil was added to the reactor followed by 413 grams of xylene solvent. The sediment in the product was then removed by centrifugation. The xylene solvent in the product was distilled by heating the product to 204° C. over approximately 45 minutes at 30 millimeters Hg vacuum and holding the product at 204° C. and 30 millimeters Hg vacuum for 10 minutes. The vacuum was replaced with nitrogen gas and the contents allowed to cool to room temperature to obtain the overbased sulfonate having the following properties based on the total weight of the product:

The weight % of calcium was 16.2, TBN was 429, weight % of sulfur was 1.70, weight % of calcium sulfonate was 0.94, and viscosity was 111 cSt at 100° C.

What is claimed is:

1. A process for preparing an alkylated aromatic composition comprising contacting at least one aromatic hydrocarbon with at least one olefin in the presence of a zeolite catalyst having a macropore structure comprising zeolite Y and mordenite zeolite, wherein the mordenite zeolite has a silica to alumina molar ratio of about 50:1 to about 105:1, and wherein the peak macropore diameter of the catalyst, measured by ASTM Test No. D 4284-03, is less than or equal to about 2000 angstroms and the cumulative pore volume of the catalyst at pore diameters less than or equal to about 500 angstroms, measured by ASTM Test No. D 4284-03, is less than or equal to about 0.30 milliliters per gram.

2. The process of claim 1 wherein the cumulative pore volume of the zeolite catalyst at pore diameters less than or equal to about 400 angstroms is less than or equal to about 0.30 milliliters per gram.

3. The process of claim 2 wherein the cumulative pore volume zeolite catalyst at pore diameters less than or equal to about 300 angstroms is less than or equal to about 0.25 milliliters per gram.

4. The process of claim 3 wherein the cumulative pore volume zeolite catalyst at pore diameters less than or equal to about 300 angstroms is less than or equal to about 0.20 milliliters per gram.

5. The process of claim 4 wherein the cumulative pore volume of the zeolite catalyst at pore diameters less than or equal to about 400 angstroms is in the range of about 0.05 milliliters per gram to about 0.18 milliliters per gram.

6. The process of claim 5 wherein the cumulative pore volume of the zeolite catalyst at pore diameters less than or equal to about 300 angstroms is in the range of about 0.08 milliliters per gram to about 0.16 milliliters per gram.

7. The process of claim 1 wherein the peak macropore diameter of the zeolite catalyst is in the range of about 400 angstroms to about 1500 angstroms.

8. The process of claim 7 wherein the peak macropore diameter of the zeolite catalyst e is in the range of about 500 angstroms to about 1300 angstroms.

9. The process of claim 8 wherein the peak macropore diameter of the zeolite catalyst is in the range of about 600 angstroms to about 1100 angstroms.

10. The process of claim 9 wherein the peak macropore diameter of the zeolite catalyst is in the range of about 750 angstroms to about 900 angstroms.

11. The process of claim 1 wherein the zeolite Y has a silica to alumina molar ratio of about 5:1 to about 100:1 and the mordenite zeolite has a silica to alumina molar ratio of about 50:1 to about 105:1.

12. The process of claim 11 wherein the zeolite Y has a silica to alumina molar ratio of about 30:1 to about 90:1.

13. The process of claim 12 wherein the zeolite Y and the mordenite zeolite independently have a silica to alumina molar ratio of about 60:1 to about 80:1.

14. The process of claim 1 wherein the zeolite catalyst contains a binder.

15. The process of claim 14 wherein the binder is alumina.

16. The process of claim 1 wherein the zeolite catalyst is in the form of a tablet.

* * * * *